(12) United States Patent
Newby et al.

(10) Patent No.: US 6,440,104 B1
(45) Date of Patent: *Aug. 27, 2002

(54) SAFETY SHIELD ASSEMBLY

(75) Inventors: C. Mark Newby, Tuxedo, NY (US); Michael C. Bennett, Summit, NJ (US); Jamie Crawford, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,976

(22) Filed: Aug. 23, 1999

Related U.S. Application Data

(60) Provisional application No. 60/098,282, filed on Aug. 28, 1998.

(51) Int. Cl.$^7$ .............................................. A61M 5/32
(52) U.S. Cl. ..................... 604/192; 604/110; 604/263; 128/919
(58) Field of Search ............................... 604/181–182, 604/188, 192, 197–199, 272, 239–241, 243, 110, 187, 263, 905; 128/919

(56) References Cited

U.S. PATENT DOCUMENTS

| | | | |
|---|---|---|---|
| 2,408,323 A | 9/1946 | Lockhart | |
| 3,306,290 A | 2/1967 | Weltman | |
| 3,658,061 A | 4/1972 | Hall | |
| 4,085,737 A | 4/1978 | Bordow | |
| 4,747,836 A | 5/1988 | Luther | |
| 4,834,715 A | 5/1989 | Hanifl | |
| 4,886,503 A | 12/1989 | Miller | |
| 4,944,397 A | 7/1990 | Miller | |
| 4,950,249 A | 8/1990 | Jagger | |
| 4,966,591 A | 10/1990 | Yuen | |
| 4,982,842 A | 1/1991 | Hollister | |
| 5,055,102 A | 10/1991 | Sitnik | |
| 5,084,027 A * | 1/1992 | Bernard | |
| 5,116,325 A | 5/1992 | Paterson | |
| 5,135,509 A | 8/1992 | Olliffe | |
| 5,139,489 A * | 8/1992 | Hollister | |
| 5,151,089 A | 9/1992 | Kirk, III | |
| 5,154,285 A | 10/1992 | Hollister | |
| 5,188,611 A | 2/1993 | Orgain | |
| 5,207,653 A | 5/1993 | Janjua | |
| 5,312,367 A | 5/1994 | Nathan | |
| 5,423,765 A | 6/1995 | Hollister | |
| 5,437,648 A | 8/1995 | Graves | |
| 5,445,619 A | 8/1995 | Burns | |
| 5,490,841 A | 2/1996 | Landis | |
| 5,509,907 A | 4/1996 | Bevilacqua | |
| 5,584,816 A | 12/1996 | Gyure | |
| 5,599,318 A * | 2/1997 | Sweenet et al. | |
| 5,615,771 A | 4/1997 | Hollister | |
| 5,632,732 A | 5/1997 | Szabo | |
| 5,643,219 A | 7/1997 | Burns | |
| 5,649,622 A | 7/1997 | Hollister | |
| 5,662,617 A | 9/1997 | Odell | |
| 5,665,075 A * | 9/1997 | Gyure et al. | |
| 5,669,889 A | 9/1997 | Gyure | |
| 5,681,295 A | 10/1997 | Gyure | |
| 5,807,351 A | 9/1998 | Kashmer | |
| 5,868,716 A * | 2/1999 | Sweeney et al. | |
| 6,298,541 B1 * | 10/2001 | Newby et al. | 29/451 |

FOREIGN PATENT DOCUMENTS

| | | |
|---|---|---|
| EP | 460821 A1 | 5/1991 |
| EP | 566631 B1 | 11/1991 |
| EP | 520930 A1 | 5/1992 |
| EP | 0 623 358 A2 | 11/1994 |
| WO | WO93/1299 | 7/1993 |

\* cited by examiner

Primary Examiner—Brian L. Casler
Assistant Examiner—LoAn H. Thanh
(74) Attorney, Agent, or Firm—Nanette S. Thomas, Esq.

(57) ABSTRACT

The present invention is a safety shield assembly having a shield and a collar for connecting the shield to a fluid handling device whereby the shield may be pivoted with respect to the collar. Preferably, the safety shield assembly may be used with a needle assembly, an intravenous infusion set a syringe, a catheter or other fluid handling devices or assemblies that contain piercing elements.

43 Claims, 16 Drawing Sheets

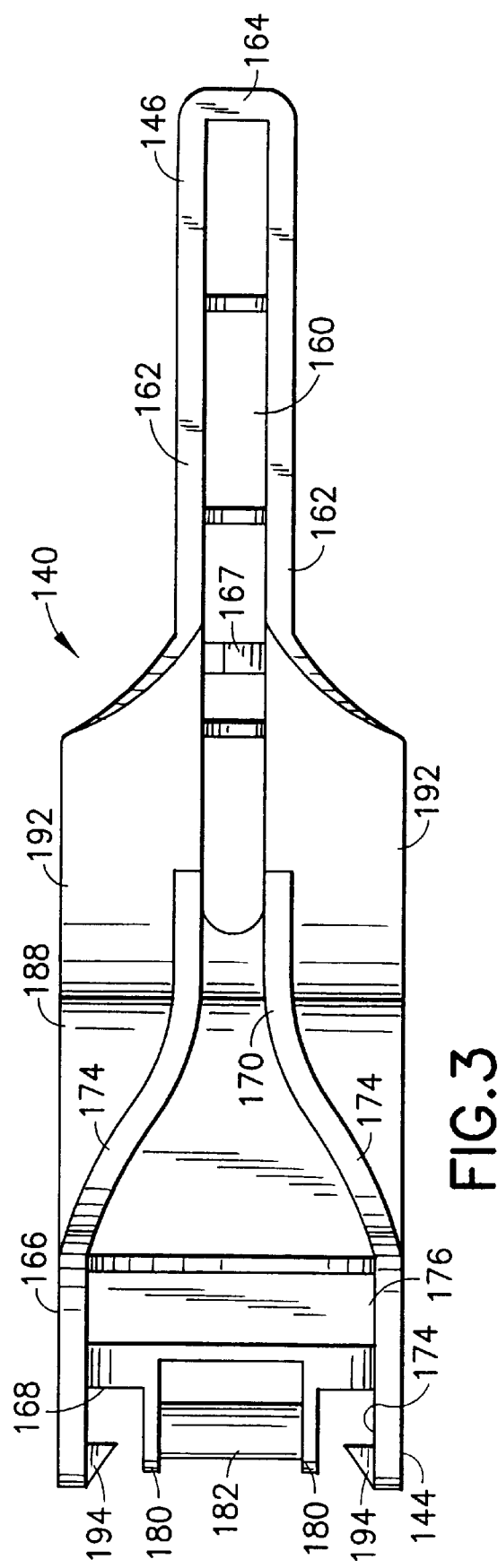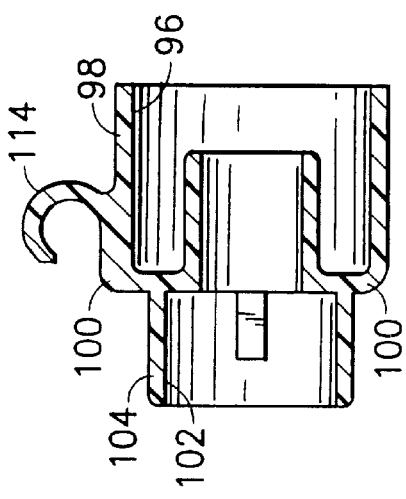

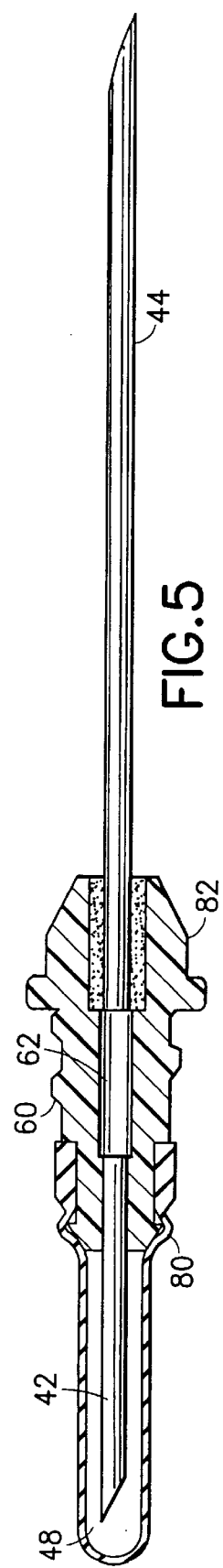
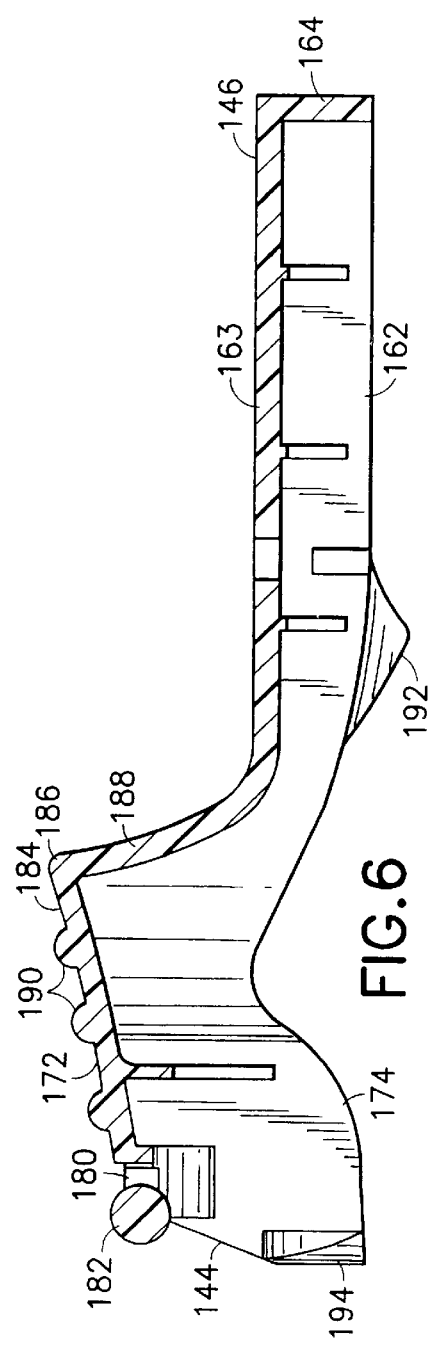

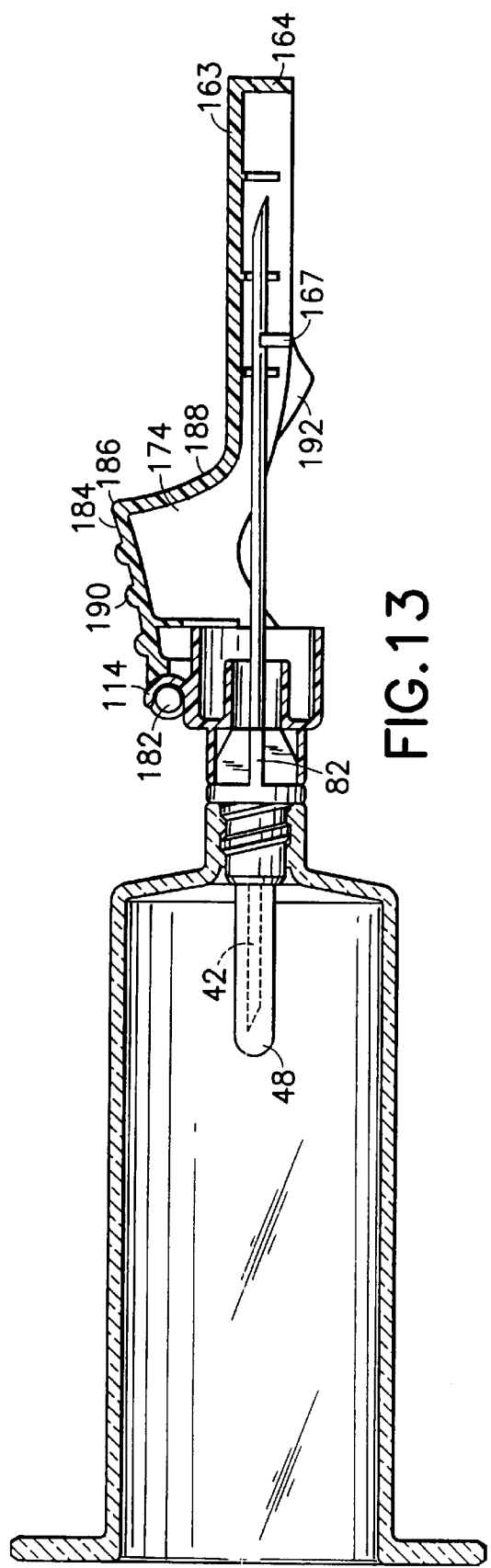
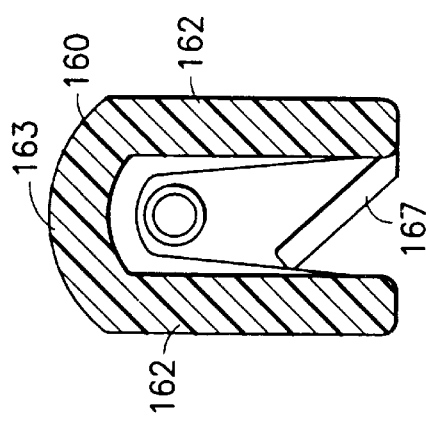
FIG. 13
FIG. 14

SAFETY SHIELD ASSEMBLY

This application claims benefit of 60/098,282 filed Aug. 28, 1998.

BACKGROUND OF THE INVENTION

1. Field of Invention

The present invention relates to a shield for a needle and more particularly to a safety shield assembly that may be used in conjunction with a syringe assembly, a hypodermic needle, a needle assembly, a needle assembly with a needle holder, a blood collection needle, a blood collection set, an intravenous infusion set or other fluid handing devices or assemblies that contain piercing elements.

2. Description of Related Art

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannula or blunt ended cannula.

Safe and convenient handling of disposable medical devices is recognized by those in the medical arts so as to minimize exposure to blood borne pathogens. Safe and convenient handling of disposable medical devices results in the disposal of the medical devices intact.

As a result of this recognition, numerous devices have been developed for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies.

Therefore, there exists a need for a safety shield assembly: (i) that is easily manufactured; (ii) that is applicable to many devices; (iii) that is simple to use with one hand; (iv) that can be safely disposed of; (v) that does not interfere with normal practices of needle use; (vi) that has tactile features whereby the user may be deterred from contacting the needle, the user may easily orient the needle with the patient and easily actuate and engage the shield assembly; (vii) that has visual features whereby the user may be deterred from contacting the needle, the user may easily orient the needle with the patient and easily actuate and engage the shield assembly; (viii) that is not bulky; (ix) that includes means for minimizing exposure to the user of residual fluid leaking from the needle; and (x) provides minimal exposure to the user because the needle shield is immediately initiated by the user after the needle is withdrawn from the patient's vein.

SUMMARY OF THE INVENTION

The present invention is a safety shield assembly, the method for assembling the safety shield assembly, and the method for using the safety shield assembly in a fluid handling procedure.

The assembly of the present invent ion preferably comprises, a shield, means for connecting the shield to a fluid handling device that contains a piercing element such as needle, means for pivoting the shield away from the needle, means for securely covering and/or containing the needle within the shield and means for securely locking the shield in a final non-retractable closed position over the needle.

Preferably, the shield comprises a rearward end, a forward end, a slot or longitudinal opening for housing the used needle in the forward end, means for securing the needle in the slot, means for guiding the needle into the slot, means for connecting the shield and the fluid handling device, means for guiding the user's fingers to move the shield into various positions, and means for retaining the shield securely over the used needle.

Desirably, the means for connecting the shield to the fluid handling device is with a collar. Preferably, the shield is movably connected to a collar which is connected to a fluid handling device.

Preferably, the shield is connected to the collar by a hanger bar that engages with a hook arm that is located on the collar so that the shield may be pivoted with respect to the collar and the shield is able to easily move into several positions. It is within the purview of the present invention to include any structure for connecting the shield to the collar so that the shield may be pivoted with respect to the collar. These structures include known mechanical hinges and various linkages, living hinges, or combinations of hinges and linkages.

Most preferably, the shield is connected to the collar by an interference fit between the hanger bar and the hook bar. Therefore, the shield is always oriented in a stable position and will not move forward or backwards unless movement of the shield is relative to the hanger bar and the hook bar is positively initiated by the user.

Alternatively, it is within the purview of the present invention that the shield and collar is unitary one-piece structure. The one-piece structure may be accomplished by many methods including molding the shield and the collar as a one-piece unit thereby eliminating the shield and the collar during the manufacturing process.

The assembly of the present invention may further comprise tactile and visual means for deterring the user from contacting the needle, providing easy orientation of the needle with the patient and provide the user with a guide for actuation and engagement with the shield.

The assembly of the present invention may further comprise means for minimizing exposure by the user to residual fluid leaking from a used needle, whereby a polymer material is located in the shield. Desirably, the material may be a gel like material.

Most desirably, the assembly of the present invention is such that the cooperating parts of the assembly provide the means for the shield to move into a forward use position over the needle. Thus, by simple movement of the shield into a positive position over the used needle, the assembly is ready for subsequent disposal. Therefore, the safety shield assembly of the present invention provides minimal exposure of the user to a needle because the shield is immediately initiated by the user after the needle is withdrawn from the patient's vein.

Desirably, the assembly of the present invention may be used with a syringe assembly, a hypodermic needle, a needle assembly, a needle assembly with a needle holder, a blood collection set, an intravenous infusion set or other fluid handling devices. Preferably, the assembly of the present invention is used with a needle assembly comprising a needle and a hub. Preferably the needle is a conventional double ended needle.

Most preferably, the present invention is used with a needle assembly comprising a hub and a needle connected to the hub whereby the needle comprises a non-patient end and an intravenous end. The collar of the present invention is connected to the hub, which comprises a hook arm and the shield is movably connected to the hook arm whereby the shield may be pivoted with respect to the collar and easily moved into several positions.

Preferably, the collar is fitted with the hub of the needle assembly whereby the collar cannot rotate around the hub. Additionally, the collar includes cooperating means that mate with reciprocal means on the shield to lock the shield in a final closed position.

Alternatively, it is within the purview of the present invention that the collar and hub is a unitary one-piece structure. The one piece structure may be accomplished by many methods including molding the collar and the hub as a one-piece unit thereby eliminating the need to separately assemble the collar to the hub during the manufacturing process.

Most preferably, the collar is fitted with the hub of the needle assembly whereby the bevel surface or bevel up surface of the intravenous end of the needle faces the same side of the collar when the shield is in the open position. Alignment of the collar, hub, shield and needle with the bevel surface up makes it easier to insert the needle into the patient without manipulating the assembly. The orientation of the intravenous end of the needle as bevel up assures the user that the needle is properly oriented for use and does not require any manipulation before use. Most notably, the orientation of the shield provides a visual indication to the user of the orientation of the bevel surface of the needle.

Preferably, the shield is capable of pivoting from an open position where the intravenous end of the needle is exposed and bevel up, to an intermediate position where the needle is partially covered, to a final closed nonretractable position where the needle is completely covered and the shield is locked and no longer able to be move out of the closed position.

Alternatively, it is within the purview of the present invention that the shield, collar and hub is a unitary one-piece structure. The one-piece structure may be accomplished by many methods including molding the shield, collar and hub as a one-piece unit thereby eliminating the need to separately assemble the shield, collar and hub during the manufacturing process.

It is an advantage of the present invention that the shield covering the used intravenous end of the needle provides easy containment of the used needle. A further advantage of the shield is that it will not only move upon initiation by the user.

The assembly of the present invention when used with a fluid handling device is also easily disposable when removed from a conventional needle holder, or other such device.

Another important feature of the present invention includes means for locking the shield in a closed permanent position covering the needle. The closed permanent position will generally withstand the normal forces encountered during proper disposal of the safety shield assembly when it is removed from a conventional needle holder.

A notable attribute of the present invention is that it is easily adaptable with many devices. For example, with syringe assemblies, hypodermic needles, needle holders, blood collection needles, blood collection sets, intravenous infusion sets such as catheters or other fluid handling devices or assemblies that contain piercing elements.

Another notable attribute of the present invention is that the tactile and visual features deter the user from touching the needle, allow the user to easily orient the needle with the patient and guide the user to actuate and engage the shield of the assembly.

DESCRIPTION OF THE DRAWINGS

FIG. 3 is a bottom view of the shield as shown in FIG. 2.

FIG. 4 is a cross sectional view of the collar as shown in of FIG. 2 taken along lines 4—4 thereof.

FIG. 5 is a cross sectional view of the needle hub as shown in FIG. 2 taken along lines 5—5 thereof.

FIG. 6 is a cross sectional view of the shield of FIG. 2 taken along lines 6—6 thereof.

FIG. 13 is a cross sectional view of the assemblies in use with a conventional needle holder as shown in FIG. 11 taken along lines 13—13 thereof.

FIG. 14 is a cross-sectional view of the assemblies of FIG. 11 taken along lines 14 —14 thereof.

DETAILED DESCRIPTION

Figure 1:
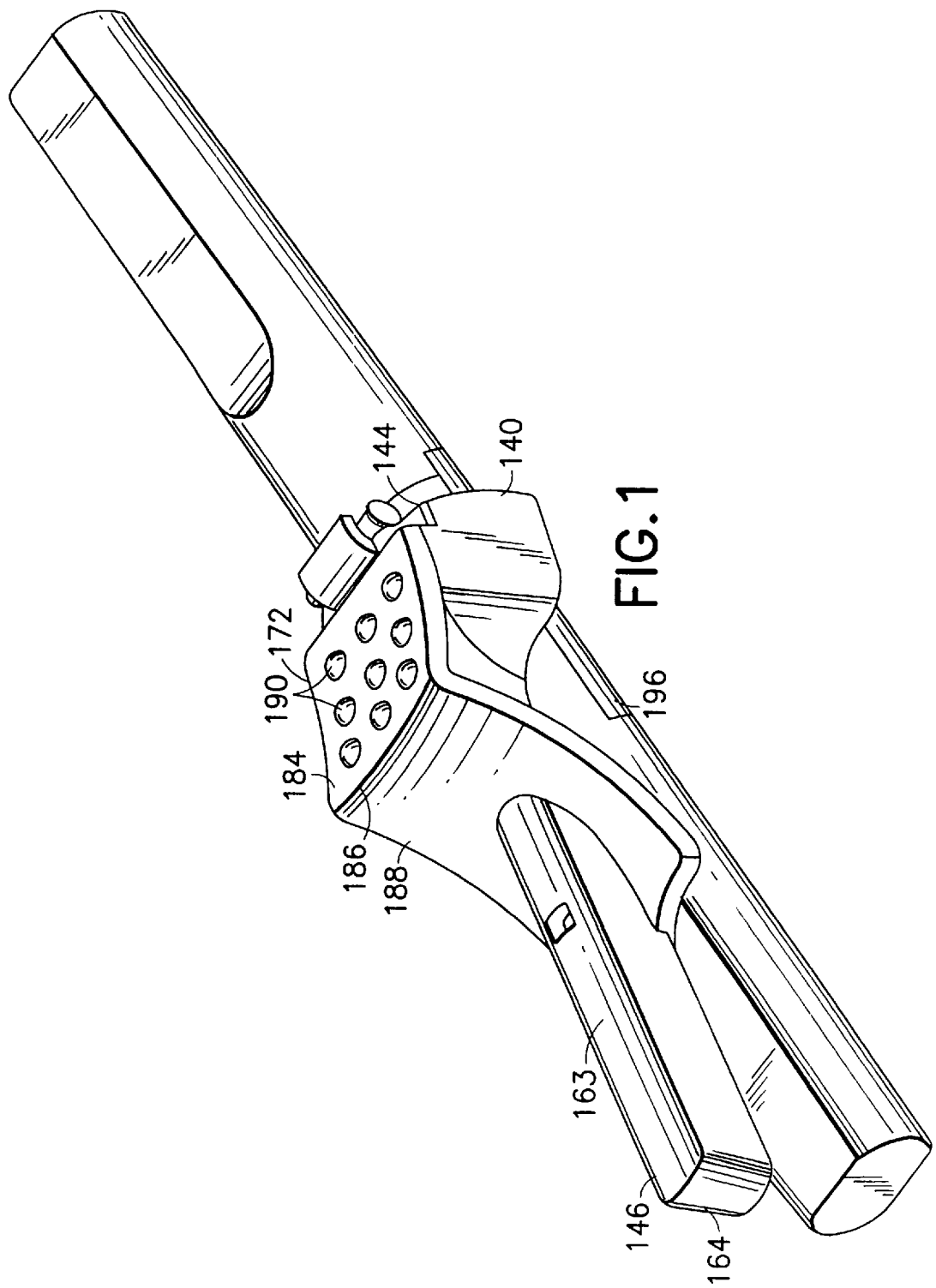
FIG. 1 is a perspective view of the safety shield assembly of the present invention connected to a needle assembly and related packaging features.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
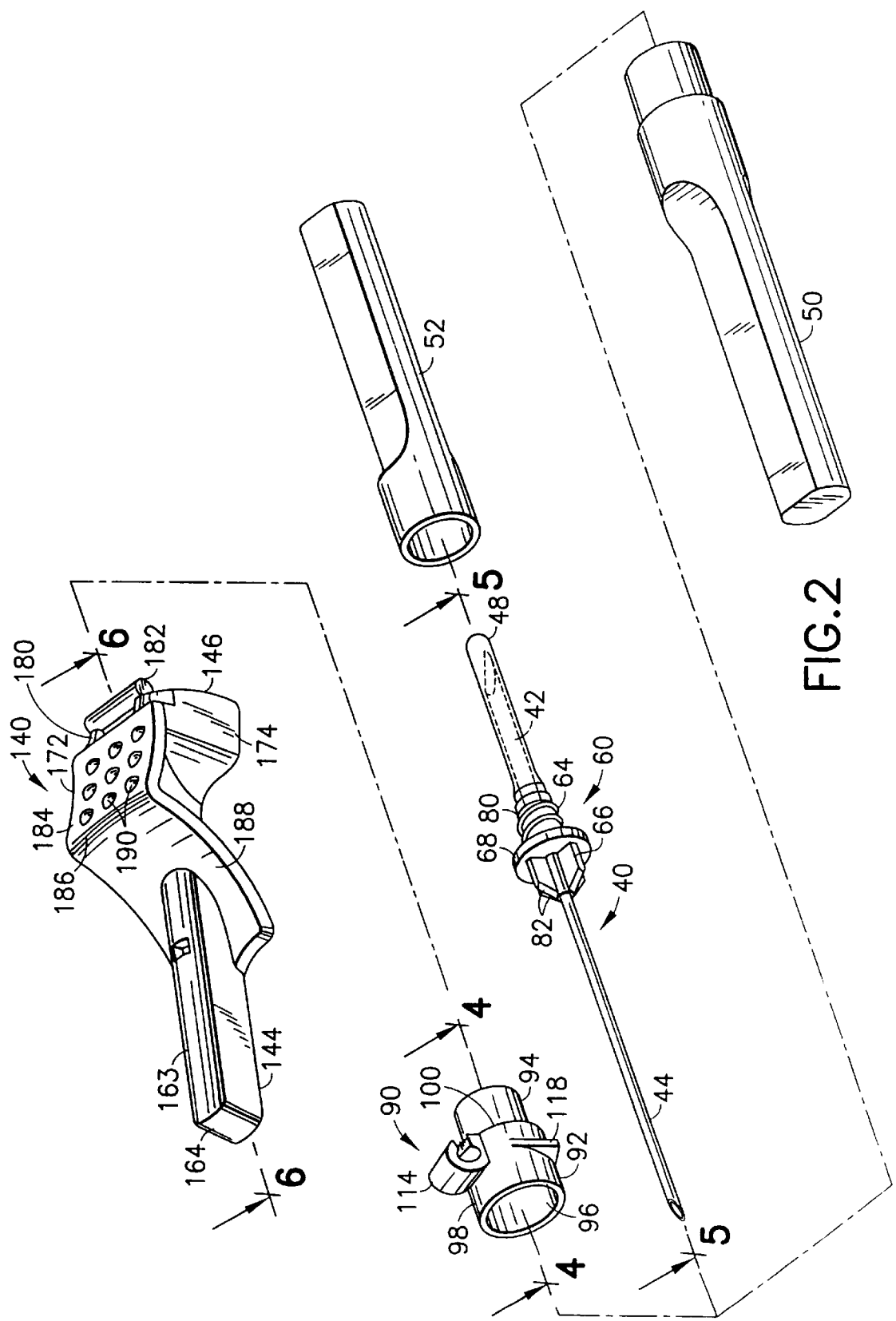
FIG. 2 is a perspective view of the unassembled pieces of FIG. 1.
Figure 7:
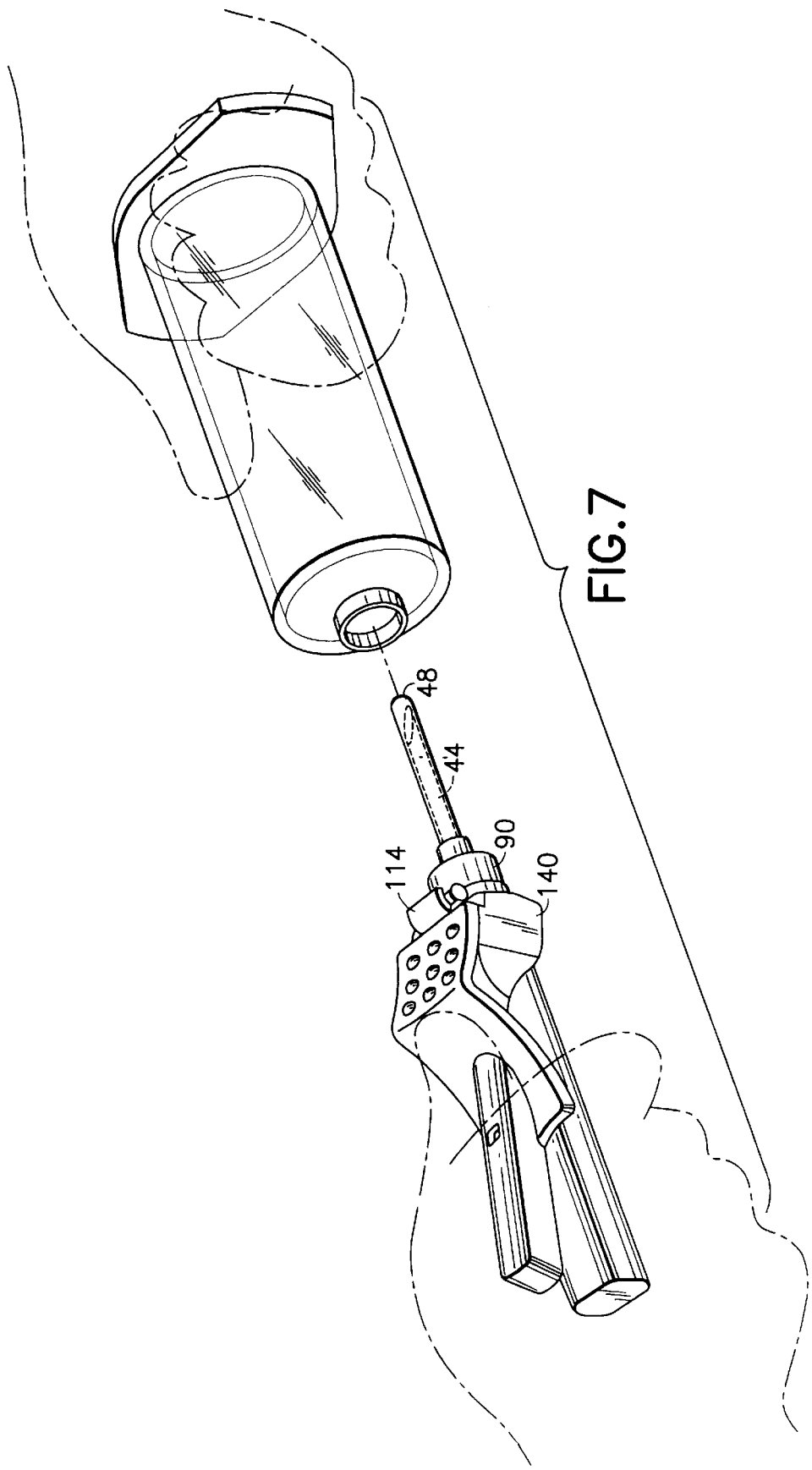
FIGS. 7–11 illustrate the use of the safety shield assembly with the needle assembly of FIG. 1 with a conventional needle holder.
Figure 8:
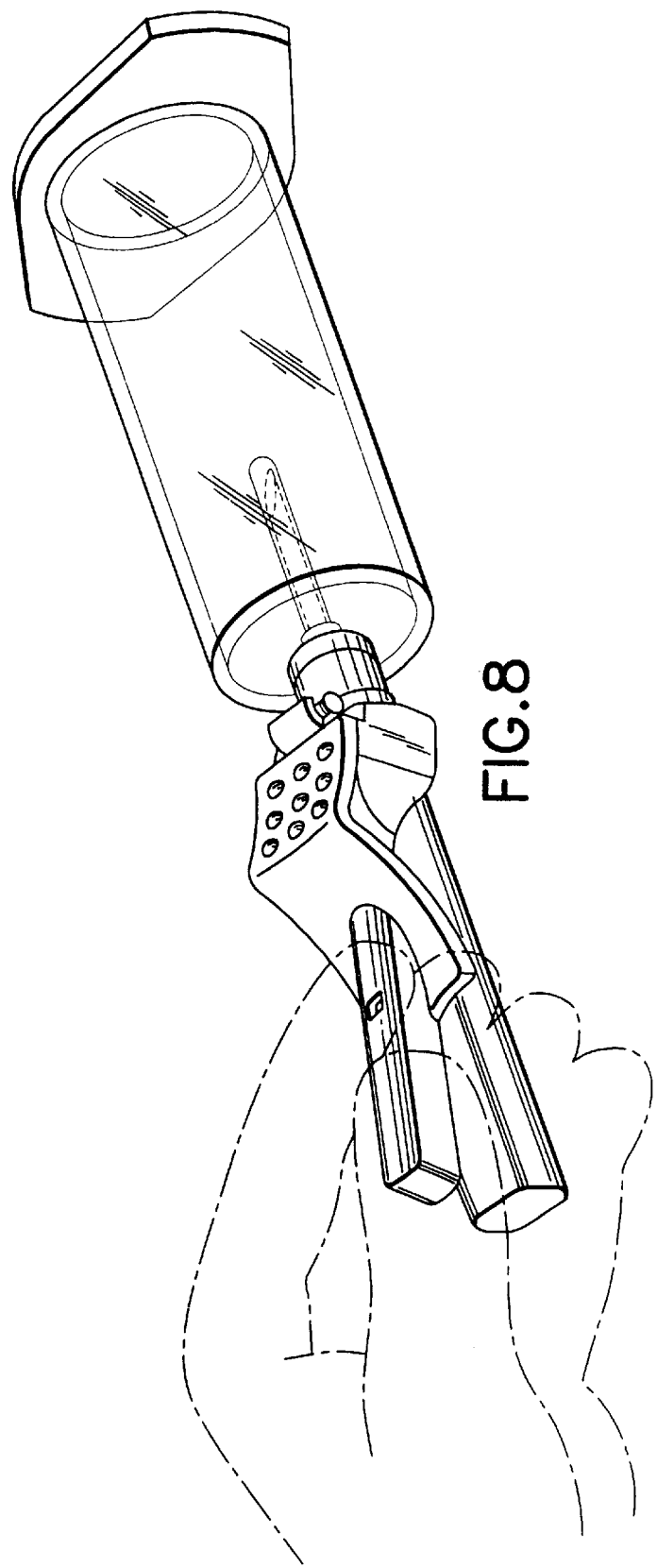

Referring to the drawings in which like reference characters refer to like parts throughout the several views thereof, FIGS. 1 and 2 illustrate a needle assembly with the safety shield assembly of the present invention and the related packaging features. The needle assembly includes a needle 40 and a hub 60 and packaging features to cover the needle and a label and the safety shield assembly includes a collar 90 and a shield 140.

As shown in FIGS. 2 and 5, needle 40 includes a non-patient end 42, an intravenous end 44 and a passageway 46 extending between the non-patient end and the intravenous end. An elastomeric sleeve 48 covers the non-patient end, a rigid sleeve 50 covers the intravenous end and a second rigid sleeve 52 covers the non-patient end and the elastomeric sleeve. As shown in FIG. 1, a label 196 may also be applied to the finally assembled parts.

As shown in FIGS. 2 and 5, hub 60 includes a threaded end 64, a ribbed end 66 and passageway 62 extending between the threaded end and the ribbed end. Threaded end 64 and ribbed end 66 are separated by flange 68. Non-patient end 42 of needle 40 extends from threaded end 64 and intravenous end 44 of needle 40 extends from ribbed end 66. Preferably, threaded end 64 comprises male threads 80 for mounting the hub on a conventional needle holder and ribbed end 66 comprises male ribs 82 for connecting the hub and collar 90.

As shown in FIGS. 2 and 4, collar 90 includes two sections, a forward annular skirt 92 and a rearward annular skirt 94. The forward annular skirt is cylindrical comprising an inner sidewall 96 and an outer sidewall 98 and mates with the rearward annular skirt at a shoulder 100. Rearward annular skirt 94 is cylindrical comprising an inner sidewall 102 and an outer sidewall 104 and extends from shoulder 100 opposite of forward annular skirt 92. The inner diameter of forward annular skirt 92 is larger than the inner diameter of rearward annular skirt 94. Alternatively, the inner diameters for collar 90 can be formed as a constant inner diameter of the same.

Extending on outer sidewall 98 of forward skirt section 92 is a hook member 114 and located opposite or downwardly of hook member 114 on outer sidewall 98 are locking dents or protrusions 118.

As shown in FIGS. 2 and 6, shield 140 comprises a rearward end 144 and a forward end 146.

Forward end 146 of shield 140 includes a slot or longitudinal opening 160 formed by sidewalls 162 that extend downwardly from top section 163 and run substantially opposite of one another in parallel along the length of slot 160 towards forward end sidewall 164. Means for trapping a needle in slot 160 includes an arm 167 that is located at one of sidewalls 162 to secure the used needle.

Arm 167 is deflectable by the needle when the needle enters slot 160. Once the needle passes the end of the arm, the arm moves back to its original position, whereby the needle is permanently trapped in slot 160 by arm 167.

At rearward end 144 of the shield is a collar engaging area 166 that is a continuation of slot 160. Collar engaging area 166 includes a rearward end 168, a forward end 170, a top finger guide area 172, parallel sidewalls 174 that extend downwardly and inwardly from top finger guide area 172 and into sidewalls 162, an underside area 176 for surrounding collar 90, and extending arms 180 to hold hanger bar 182. Parallel sidewalls 174 include an inner surface 175 where barb dents 194 are located.

Top finger guide area 172 comprises a first ramp 184 that extends slightly on an upwardly slope from the rearward end of the collar engaging area to a shoulder 186. From shoulder 186 extends a second ramp 188 which slopes downwardly towards top section 163. Most preferably, first ramp 184 comprises touch bumps 190. The touch bumps provide a tactile and visual guide to alert the user that the user's finger has contacted the shield and that the shield is in a defined or controlled position. The touch bumps may be any configuration so long as they extend and are distinct from the top finger guide area. The touch bumps may also be of a distinguishing color as compared to the top finger guide area or the shield.

Second ramp 188 has interior surface 192 for urging the needle toward the center of slot 160 as the shield is being rotated into the closed position. The exterior surfaces are slightly inclined and extending radially from the second ramp. The interior surfaces are especially helpful if the longitudinal axis of the needle is misaligned with respect to the longitudinal axis of the hub.

Extending arms 180 are located at rearward end 168 and at the beginning of top finger area 172 and hold hanger bar 182.

Located downwardly from extending arm 180 and hanger bar 182 and on inner surface 175 of parallel sidewalls 174 are barb dents 194. The barb dents cooperate with locking dents 118 on collar 90 to secure the shield in its final locked position.

The safety shield assembly and the needle assembly are assembled together whereby needle 40 is connected to hub 60 and sealed with adhesive at the ends of the hub. Hub 60 is then joined with collar 90 by ultra-sonic welding techniques or any other bonding techniques, or mechanical fit, whereby rearward annular skirt 94 of collar 90 mates with ribbed end 66 of the hub. Male ribs 82 of the hub are contained or forced fitted within inner sidewall 102 of rearward annular skirt 94 of collar 90. The collar is aligned with the intravenous end of the needle whereby the hook arm is aligned with the bevel up of the needle. Then rigid sleeve 50 is force fitted into inner side wall 96 of forward annular skirt 92 of collar 90 to cover the needle. Thereafter, shield 140 is connected to collar 90 whereby hanger bar 182 is force fitted into hook member 114 whereby slot 160 faces rigid sleeve 50. Most preferably, the shield is connected to the collar by a force fit or interface fit between the hanger bar and the hook bar. Therefore, the shield is always oriented in a stable position and will not move unless movement of the shield is positively initiated by the user. To assemble the last piece, shield 140 is moved towards rigid sleeve 50 and second rigid sleeve 52 is force fitted onto outer sidewall 104 of rearward annular skirt 94 of collar 90.

In addition, a label 196 may be applied to the finally assembled parts. The label may be used to prevent tamper resistance of the parts, so that they are not reused.

Figure 9:
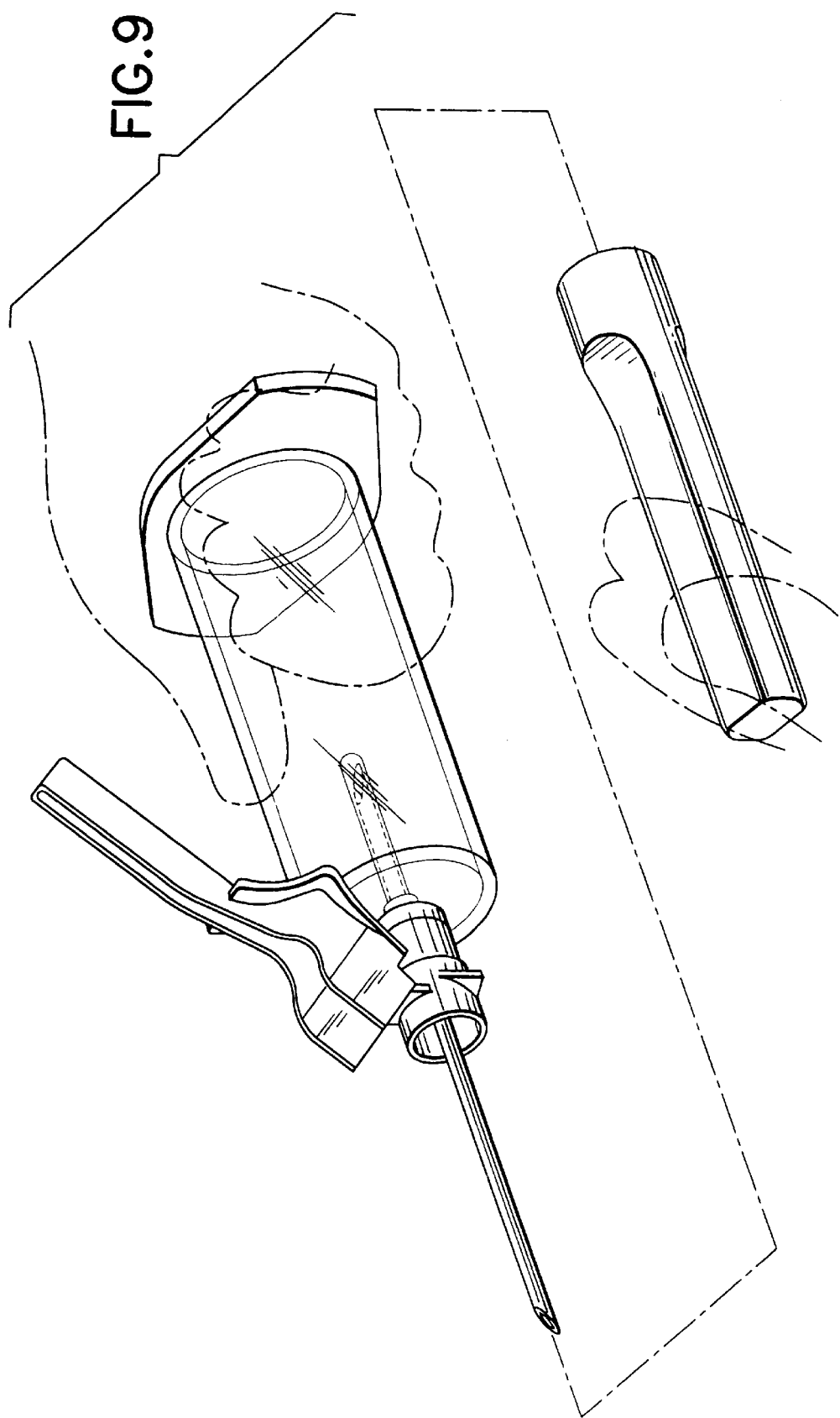
Figure 10:
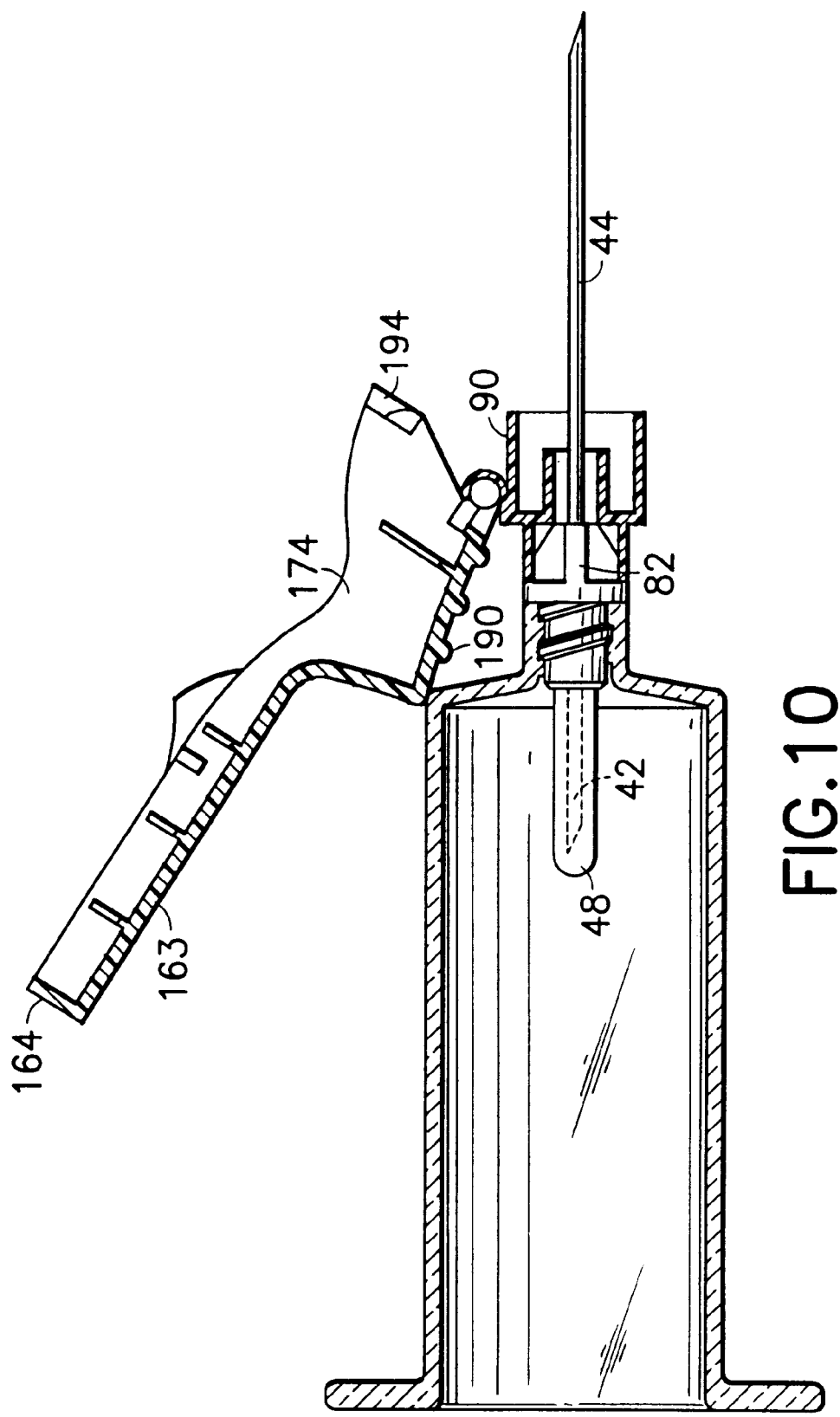
Figure 11:
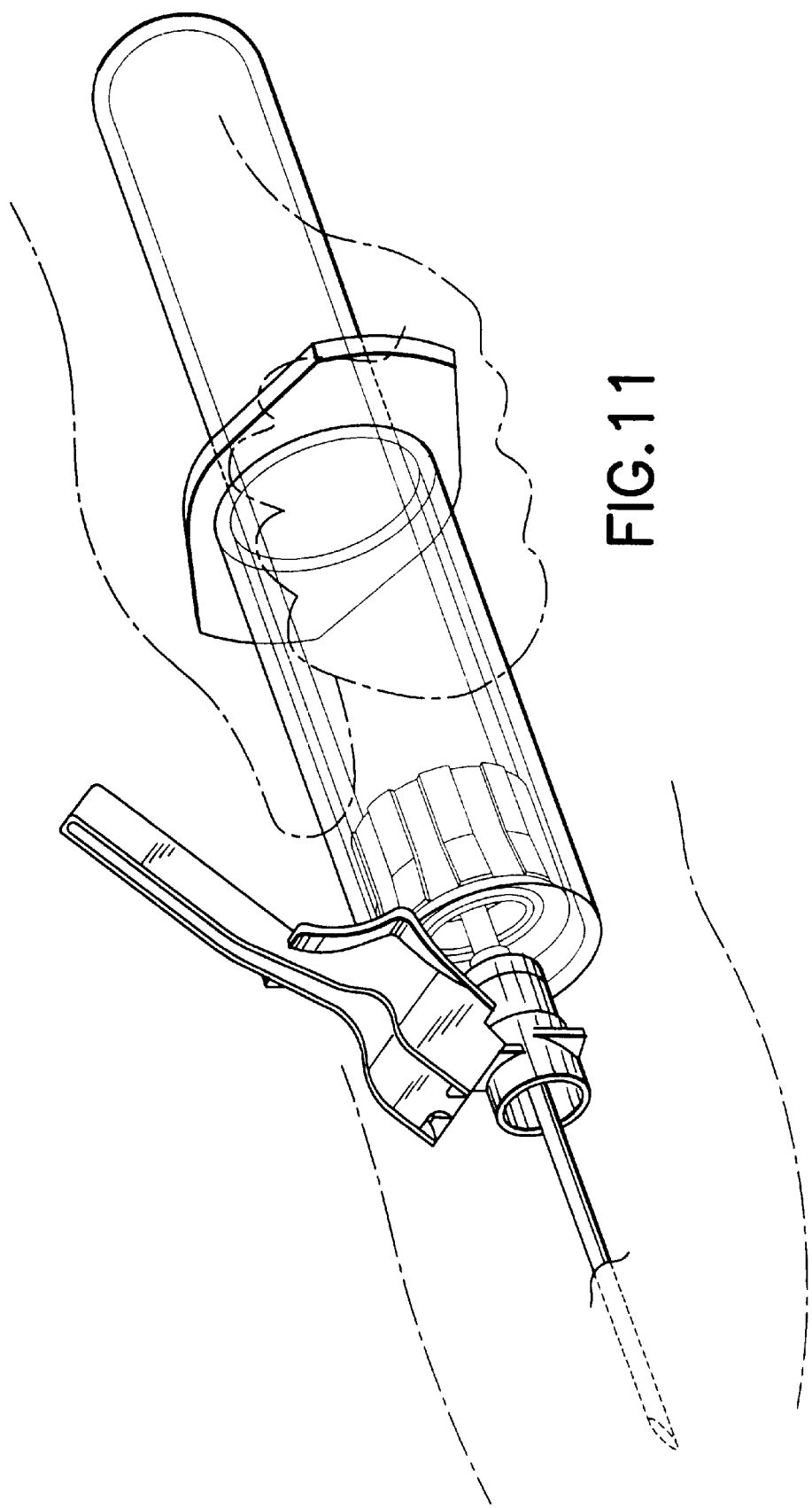
Figure 12:
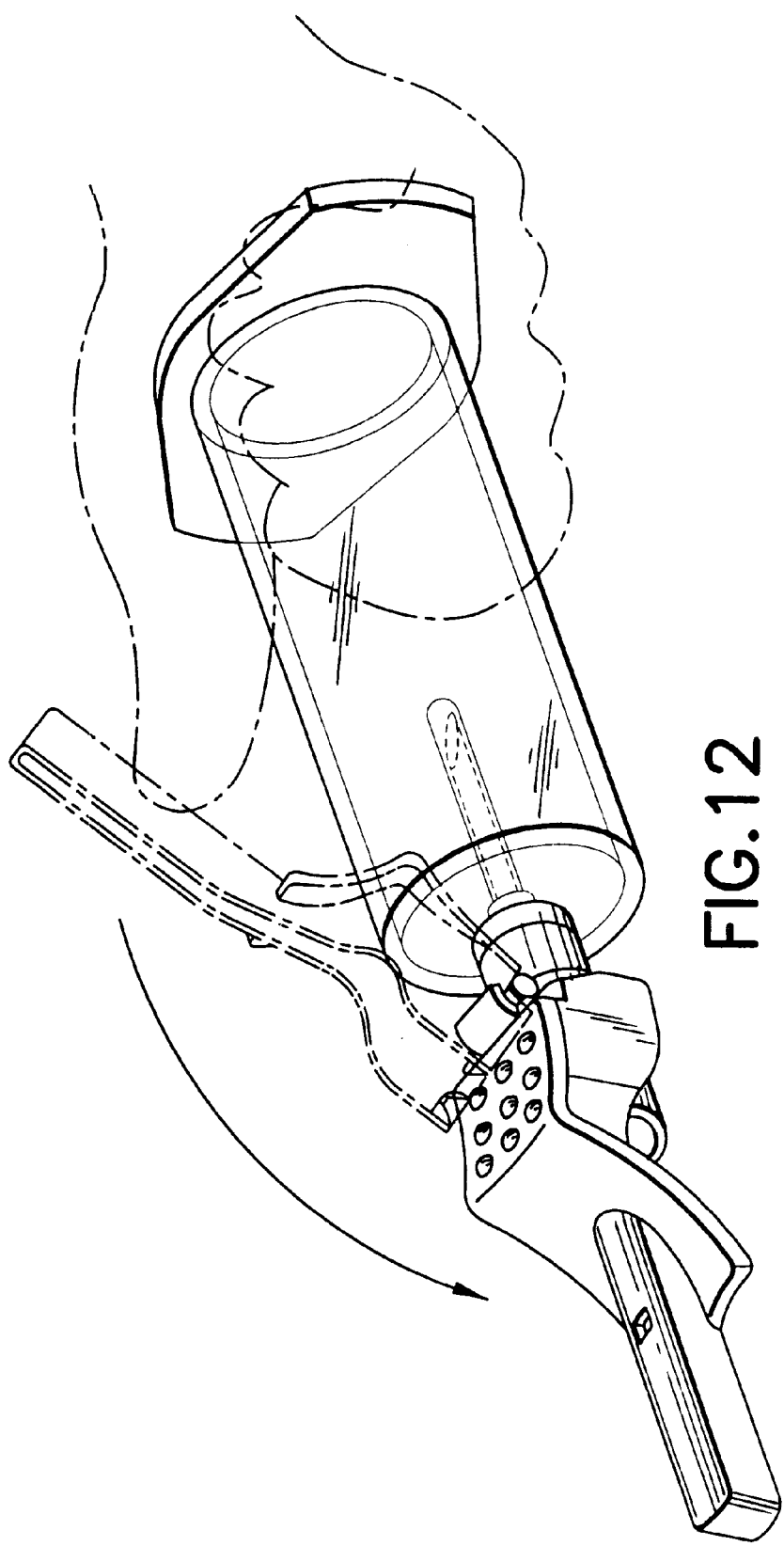
FIG. 12 is a cross sectional view of the assemblies in use with a conventional needle holder as shown in FIG. 9 taken along lines 12—12 thereof.

In use, as shown in FIGS. 7–15, the non-patient needle shield is removed and then a needle holder is screwed onto the hub of the needle. As specifically shown in FIGS. 8 and 12 the shield is then rotated back by the user towards the needle holder. Then as shown in FIG. 9, the intravenous needle shield is removed from covering the intravenous needle. Then as shown in FIG. 10, a venipuncture is conducted whereby the intravenous end of the needle is inserted into a vein of a patient and an evacuated tube having a closure is inserted into the needle holder. Then as shown in FIGS. 11 and 13, when the venipuncture is complete the user easily rotates the shield from the open position towards the intravenous needle to an intermediate position and then the user pushes on the shield at the top finger guide area to move the shield into a final, non-retractable locked position whereby the needle is trapped in the longtiudinal opening, within the arm of the needle shield and barb dents 194 of the shield are held by locking dents 118 of collar 90. As the shield is pivoted the barb dents deflect over and are held by the locking dents.

Figure 15:
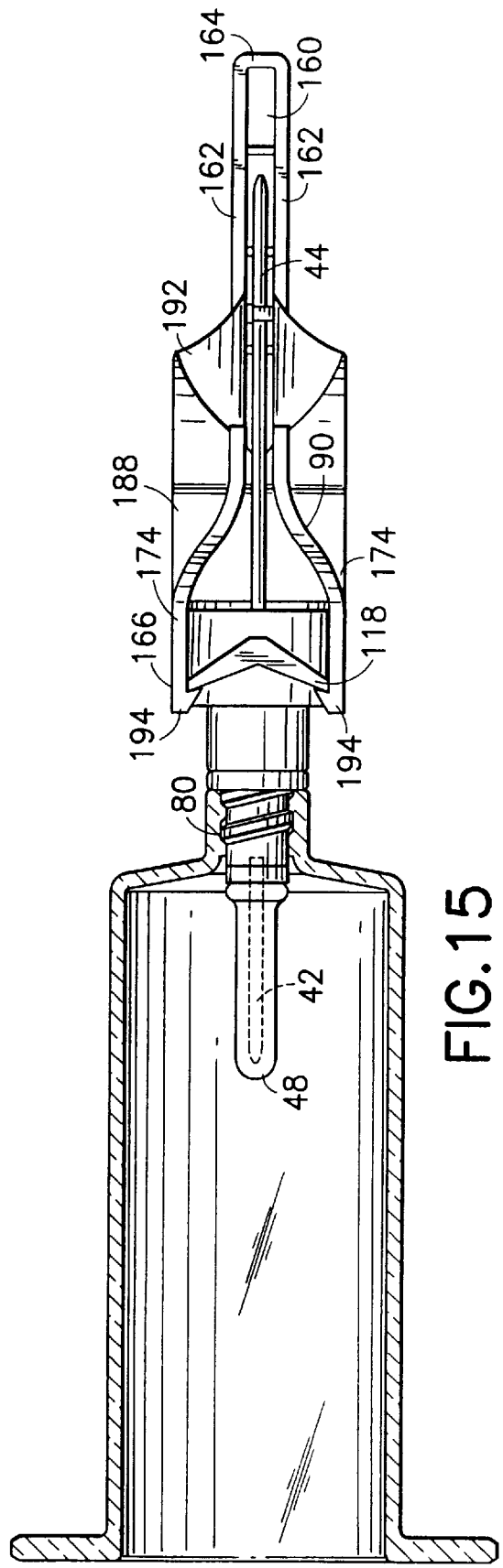
FIG. 15 is a bottom view of the assemblies as shown in FIG. 11.
Figure 16:
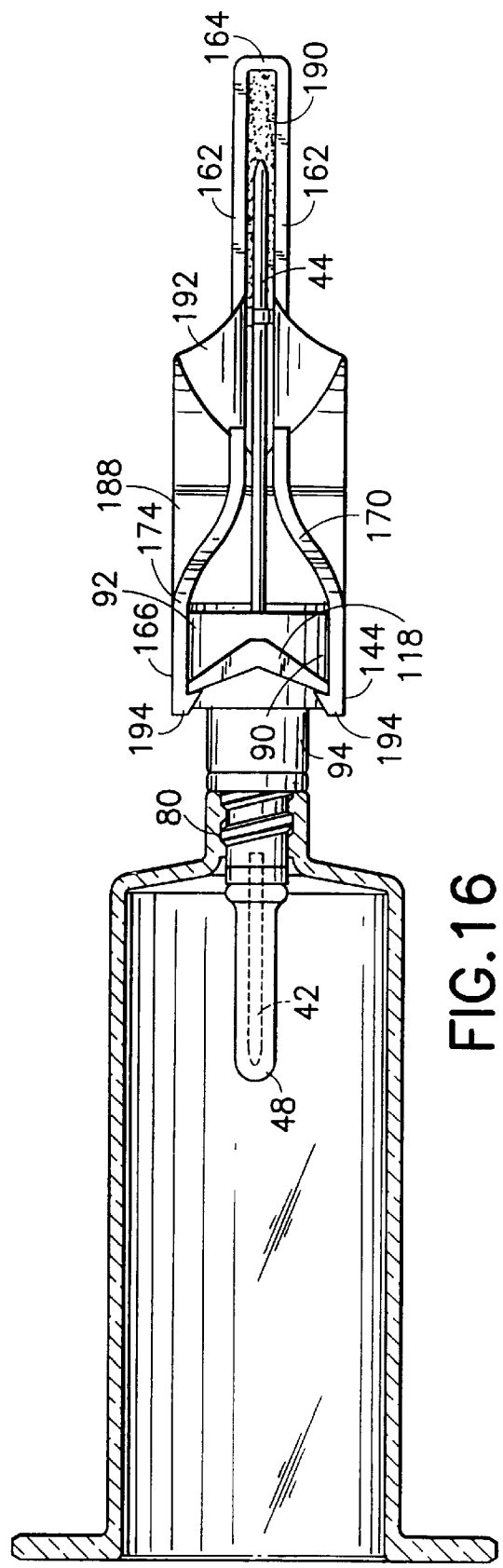
FIG. 16 illustrates an additional embodiment of the present invention, whereby a gel material is located in the shield as shown in a bottom view of the assemblies of FIG. 11.

The needle is contained within the shield as the shield is pivoted into the closed position, whereby the needle snaps past arm 167 and is trapped as shown in FIGS. 14 and 15. Alternatively as shown in FIG. 16, a gel material 190 is located in the shield near arm 167 so that when the needle snaps past arm 167 it will come to rest in gel material 190. The gel material will contain any residual fluid that may be on the needle.

Figure 17:
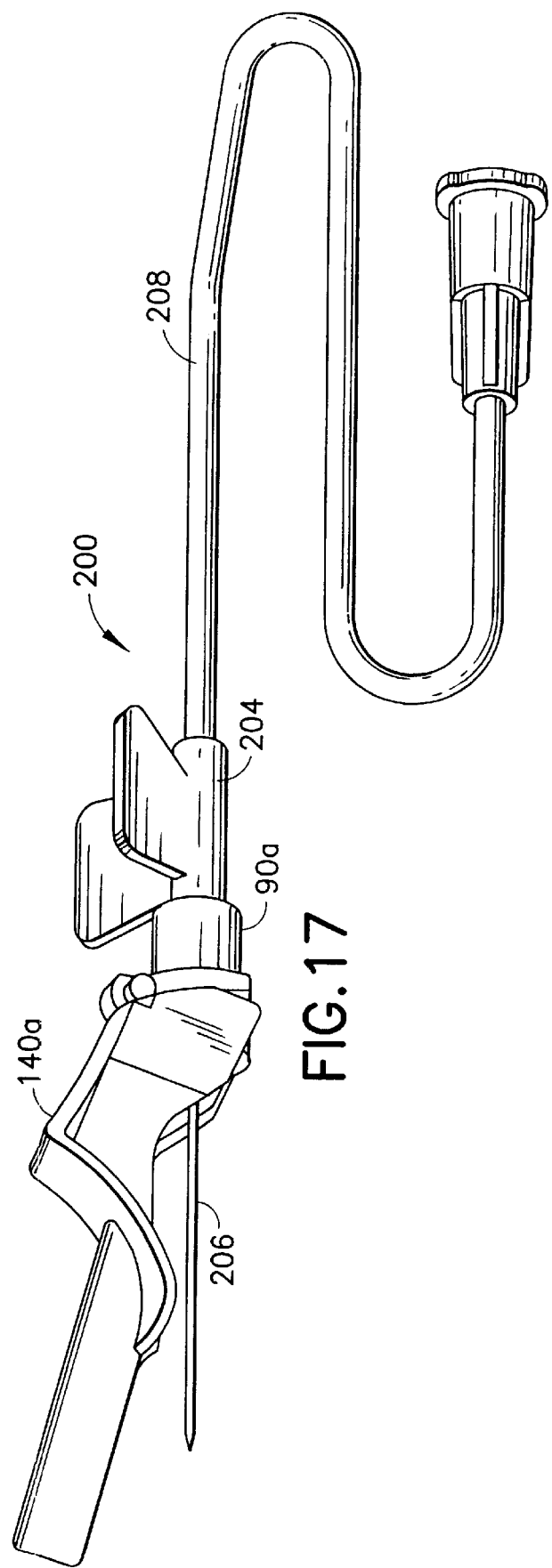
FIG. 17 is a perspective view of an additional embodiment of the present invention in use with a blood collection set.
Figure 18:
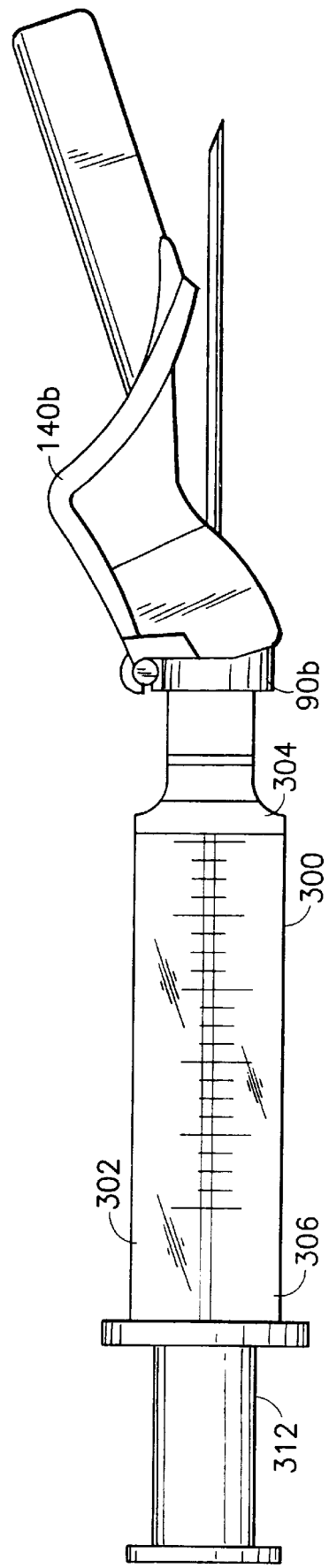
FIG. 18 is a perspective view of an additional embodiment of the present invention in use with a syringe.
Figure 19:
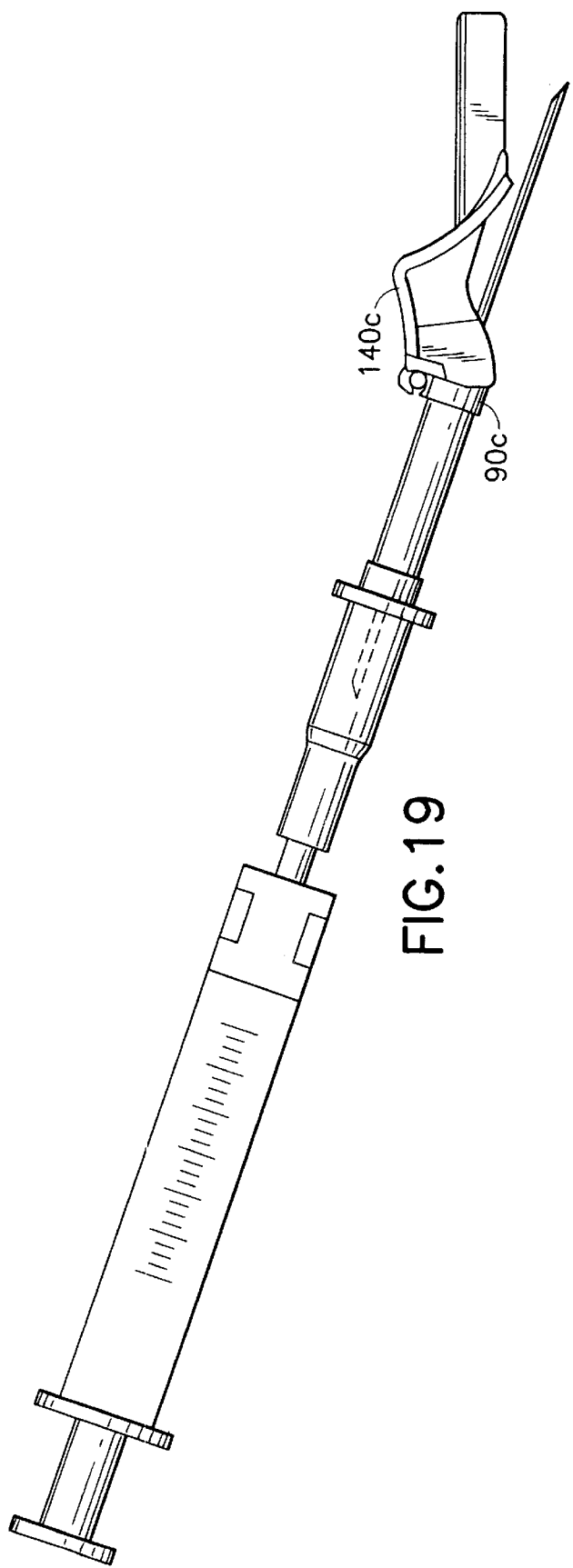
FIG. 19 is a perspective view of an additional embodiment of the present invention in use with a catheter.

FIGS. 17, 18, and 19 are further embodiments of the invention that include may components which are substantially identical to the components of FIGS. 1–3. Accordingly, similar components performing similar functions will be numbered identically to those components of FIGS. 1–3, except that a suffix "a" will be used to identify those similar components in FIG. 17, a suffix "b" will be used to identify those similar components in FIG. 18 and a suffix "c" will be used to identify those similar components in FIG. 19.

Alternatively, the safety shield assembly of the present invention may be used in conjunction with a conventional intravenous (IV) fusion set, as illustrated in FIG. 17.

For purposes of illustration, shield 140a and collar 90a are connected to a conventional IV infusion set, 200, or butterfly structure comprising a needle body with a needle hub 204 extending from the forward end of the needle body and a needle 206 embedded in hub 204. Extending from the rearward end of the needle body is flexible tubing 208 which is conventional and utilized to allow the user to manipulate the structure and to connect it subsequently to supplies of infusion liquids or for the return of collected blood if the arrangement is being used to collect blood.

Infusion set 200 further comprises flexible wings 210 attached to and projecting outwardly from needle hub 204.

Alternatively, the safety shield assembly of the present invention may be used in conjunction with a syringe, as illustrated in FIG. 18.

For purposes of illustration, shield 140b and collar 90b are connected to a conventional hypodermic syringe 300 comprising a syringe barrel 302 having a distal end 304 a proximal end 306 and a plunger 312.

Alternatively, the present invention may be used in conjunction with a catheter as illustrated in FIG. 19.

The shield and collar of the safety shield assembly of the present invention are comprised of moldable parts which can be mass produced from a variety of materials including, for example, polyethylene, polyvinyl chloride, polystryene or polyethylene and the like. Materials will be selected which will provide the proper covering and support for the structure of the invention in its use, but which will provide also a degree of resiliency for the purpose of providing the cooperative movement relative to the shield and the collar of the assembly.

What is claimed:

1. A safety shield assembly comprising:
   a shield; means for connecting said shield to a fluid handling device that contains a piercing element; means for pivoting said shield with respect to said piercing element; means for securely covering and/or containing said piercing element within said shield; and means for securely locking said shield in a final non-retractable closed position over said piercing element;
   wherein said means for connecting said shield to a fluid handling device is a collar;
   said means for pivoting said shield is the cooperation of hook arm on said collar and a hanger bar on said shield;
   said means for security locking said shield in a final non-retractable position are cooperating barb dents on said shield and said collar.

2. The assembly of claim 1, wherein said shield comprises a rearward end, a forward end, a slot or longitudinal opening for housing said piercing element in said forward end, means for securing said piercing element in said slot, means for guiding said piercing element into said slot, means for connecting said shield and said fluid handling device, means for guiding the user's fingers to move said shield into various positions and means for retaining said shield over said piercing element.

3. The assembly of claim 2, wherein said means for guiding the user's fingers to move said shield into various positions is a top finger guide area comprising a first ramp that extends slightly on an upwardly slope from said rearward end of said shield to a shoulder.

4. The assembly of claim 3, wherein said means for guiding said piercing element towards said slot is a second ramp which slopes downwardly from said shoulder.

5. The assembly of claim 4, wherein said second ramp further comprises an interior surface for urging said piercing element toward the center of the slot.

6. The assembly of claim 5, wherein said second ramp further comprises exterior surfaces that are slightly inclined and extend radially from said second ramp.

7. The assembly of claim 3, wherein said first ramp comprises touch bumps.

8. The assembly of claim 2, wherein said means for securing said piercing element in said slot is an arm, whereby said arm comprises a forward end and a rearward end and said rearward end is attached to said slot, whereby said arm is deflectable by said piercing element when said piercing element enters said slot and once said piercing element passes the forward end of said arm, said arm moves back to its undeflected position.

9. The assembly of claim 1, further comprising tactile and visual means on said shield for providing the user with a guide for pivoting said shield.

10. The assembly of claim 9, further comprising means for minimizing exposure to residual fluid on a used piercing element in said shield.

11. The assembly of claim 10, where by said means for minimizing exposure to residual fluid on a used needle is a gel material in said shield.

12. The assembly of claim 1, further comprising means for minimizing exposure by the user to residual fluid on said needle.

13. The assembly of claim 12, wherein said means for minimizing exposure by the user to residual fluid or said needle is a polymer material.

14. The assembly of claim 13, where said polymer material is a gel.

15. The assembly of claim 1, wherein said shield is movably connected to said collar which is connected to said fluid handling device.

16. The assembly of claim 6, wherein said shield is connected to said collar by an interference fit between said hanger bar and said hook arm.

17. The assembly of claim 16, wherein said collar comprises a forward annular skirt having an inner surface and an outer surface, a rearward annular skirt having an inner surface and an outer surface, a means for pivoting said shield and a means for retaining said shield in a final non-retractable position.

18. The assembly of claim 1, further comprising tactile and visual means for deterring the user from contacting said piercing element.

19. The assembly of claim 1, further comprising tactile and visual means for easily orienting said piercing element with a patient.

20. A needle shield assembly and needle assembly comprising:
   a needle assembly comprising a hub and a needle connected to said hub comprising a non-patient end and an intravenous end comprising a bevel end; and a needle shield assembly connected to said needle assembly comprising a collar and a shield, whereby said collar is connected to said hub of said needle assembly and said shield is movably connected to said collar whereby said shield may be pivoted with respect to said collar and easily moved into several positions with respect to said needle;

said shield and connected to said collar by a hanger bar located on said shield and a hook arm located on said collar whereby said hanger bar engages with said hook arm so that said shield may be pivoted with respect to said collar said shield is easily moved in a final non-retractable position whereby the cooperating barb dents on said shield and said collar are engaged.

21. The assembly of claim 20, wherein said shield comprises a rearward end, a forward end, a slot or longitudinal opening for housing said intravenous end of said needle in said forward end, means for securing said intravenous end of said needle in said slot, means for guiding said intravenous end of said needle into said slot, means for connecting said shield and said collar, means for guiding the user's fingers to move said shield into various positions and means for retaining said shield over said intravenous end of said needle.

22. The assembly of claim 21, further comprising means for guiding said intravenous end of said needle to said slot.

23. The assembly of claim 22, wherein said means for guiding said intravenous end of said needle towards said slot is a second ramp which slopes downwardly from said shoulder.

24. The assembly of claim 23, wherein said second ramp further comprises an interior surface for urging said intravenous end of said needle toward the center of the slot.

25. The assembly of claim 24, wherein said second ramp further comprises exterior surfaces that are slightly inclined and extend radially from said second ramp.

26. The assembly of claim 21, wherein said means for guiding the user's fingers to move said shield into various positions is a top finger guide area comprising a first ramp that extends slightly on an upwardly slope from said rearward end of said shield to a shoulder.

27. The assembly of claim 26, wherein said first ramp comprises touch bumps.

28. The assembly of claim 21, wherein said means for securing said intravenous end of said needle in said slot is an arm, whereby said arm comprises a forward end and a rearward end and said rearward end is attached to said slot, whereby said arm is deflectable by said intravenous end of said needle when said intravenous end of said needle enters said slot and once said intravenous end of said needle passes the forward end of said arm, said arm moves back to its undeflected position.

29. The assembly of claim 20, further comprising tactile and visual means on said shield for providing the user with a guide for pivoting said shield.

30. The assembly of claim 20, wherein said shield is movable into three positions, an open position, an intermediate position and a final non-retractable position covering said intravenous end of said needle.

31. The assembly of claim 20, wherein said collar and said shield are connected to be in alignment with to said bevel up surface of said intravenous needle.

32. A safety assembly comprising:
a needle assembly comprising a hub, a needle connected to said hub comprising a non-patient end and an intravenous end comprising a bevel end;
a needle shield assembly movably connected to said needle assembly comprising a collar and a shield whereby said collar is connected to said hub of said needle assembly and said shield is connected to said collar whereby said shield may be pivoted with respect to said collar and easily moved into several positions with respect to said needle;
a needle holder having a distal end for receiving said non-patient end of said needle assembly;
wherein said shield is connected to said collar by an interference fit between a hanger bar on said shield and hook arm on said collar;
said collar comprises a forward annular skirt having an inner surface and an outer surface, a rearward annular skirt having an inner surface and an outer surface, and a means for securely locking said shield in a final non-retractable position.

33. The assembly of claim 32, wherein said shield comprises a rearward end, a forward end, a slot or longitudinal opening for housing said intravenous end of said needle in said forward end, means for securing said intravenous end of said needle in said slot, means for guiding said intravenous end of said needle into said slot, means for connecting said shield and said collar, means for guiding the user's fingers to move said shield into various positions and means for securely locking said shield over said intravenous end of said needle in a final non-retractable position said means for securely locking said shield in a final non-retractable position are cooperating barbdents on said shield and said collar.

34. The assembly of claim 33, wherein said means for guiding the user's fingers to move said shield into various positions is a top finger guide area comprising a first ramp that extends slightly on an upwardly slope from said rearward end of said shield to a shoulder.

35. The assembly of claim 34, further comprising means for guiding said intravenous end of said needle towards said slot.

36. The assembly of claim 35, wherein said means for guiding said intravenous end of said needle towards said slot is a second ramp which slopes downwardly from said shoulder.

37. The assembly of claim 36, wherein said second ramp further comprises an interior surface for urging said intravenous end of said needle toward the center of the slot.

38. The assembly of claim 37, wherein said second ramp further comprises exterior surfaces that are slightly inclined and extend radially from said second ramp.

39. The assemlby of claim 34, wherein said first ramp comprises touch bumps.

40. The assembly of claim 3, wherein said means for securing said intravenous end of said needle in said slot is an arm in said slot having a forward end and a rearward end that is attached to said slot, whereby said arm is deflectable by said intravenous end of said needle when said intravenous end of said needle enters said slot and once said intravenous end of said needle passes the forward end of said arm, said arm moves back to its undeflected position.

41. The assembly of claim 32, further comprising tactile and visual means on said shield for providing the user with a guide for pivoting said shield.

42. The assembly of claim 32, wherein said shield is movable into three positions, an open position, an intermediate position and a final non-retractable position covering said intravenous end of said needle.

43. The assembly of claim 32, wherein said collar and said shield are connected to be in alignment with said bevel up surface of said intravenous needle.

* * * * *